(12) United States Patent
Studer et al.

(10) Patent No.: US 7,628,814 B2
(45) Date of Patent: Dec. 8, 2009

(54) INTERVERTEBRAL DISC PROSTHESIS

(75) Inventors: Armin Studer, Langendorf (CH); Jason Trachsel, Ipsach (CH); Martin Wymann, Liebefeld (CH)

(73) Assignee: Synthes USA, LLC, West Chester, PA (US)

( * ) Notice: Subject to any disclaimer, the term of this patent is extended or adjusted under 35 U.S.C. 154(b) by 685 days.

(21) Appl. No.: 11/219,590

(22) Filed: Sep. 1, 2005

(65) Prior Publication Data

US 2006/0052872 A1    Mar. 9, 2006

Related U.S. Application Data

(63) Continuation of application No. PCT/CH03/00187, filed on Mar. 24, 2003.

(51) Int. Cl.
*A61F 2/44* (2006.01)
(52) U.S. Cl. ............... 623/17.11; 623/17.13; 623/17.15; 623/17.16
(58) Field of Classification Search ......... 606/247–249; 623/17.13, 17.15, 17.16; 222/492
See application file for complete search history.

(56) References Cited

U.S. PATENT DOCUMENTS

| | | | |
|---|---|---|---|
| 4,309,777 A | | 1/1982 | Patil |
| 4,759,769 A * | | 7/1988 | Hedman et al. ......... 623/17.13 |
| 5,674,294 A * | | 10/1997 | Bainville et al. ......... 623/17.16 |
| 5,716,416 A | | 2/1998 | Lin |
| 5,782,832 A | | 7/1998 | Larsen et al. |
| 5,827,328 A * | | 10/1998 | Buttermann ............ 623/17.13 |
| 6,136,031 A * | | 10/2000 | Middleton ............... 623/17.16 |
| 6,213,775 B1 * | | 4/2001 | Reipur ................... 433/173 |
| 6,447,543 B1 * | | 9/2002 | Studer et al. ............ 623/17.11 |
| 6,468,309 B1 * | | 10/2002 | Lieberman .............. 623/17.11 |
| 6,520,996 B1 * | | 2/2003 | Manasas et al. .......... 623/23.5 |
| 6,723,127 B2 * | | 4/2004 | Ralph et al. ............. 623/17.13 |
| 2003/0045940 A1 * | | 3/2003 | Eberlein et al. .......... 623/17.16 |
| 2004/0204763 A1 * | | 10/2004 | Ralph et al. ............. 623/17.13 |

FOREIGN PATENT DOCUMENTS

| EP | 0346269 B1 | 6/1989 |
|---|---|---|
| FR | 2734148 A1 | 11/1996 |

OTHER PUBLICATIONS

Chen, et al., "Stress Analysis of the Disc Adjacent to Interbody Fusion in Lumbar Spine", 2001, Medical Engineering & Physics, 23, 483-491.*

* cited by examiner

*Primary Examiner*—Thomas C Barrett
*Assistant Examiner*—David W Bates
(74) *Attorney, Agent, or Firm*—Stroock & Stroock & Lavan LLP

(57) ABSTRACT

Intervertebral disc prosthesis including an upper apposition plate appropriate to rest against the base plate of an upper vertebra, a lower apposition plate spaced apart from the upper apposition plate and suitable to rest against the base plate of a lower vertebra, a plurality of elastic devices mounted between the two apposition plates and in their peripheral zones in a manner that the two apposition plates shall be displaceable in mutually resilient manner, and a central axis which runs essentially perpendicularly to the two apposition plates, the elastic devices being designed/configured in a manner that the intervertebral disc prosthesis as a whole exhibits asymmetrical stiffness.

8 Claims, 9 Drawing Sheets

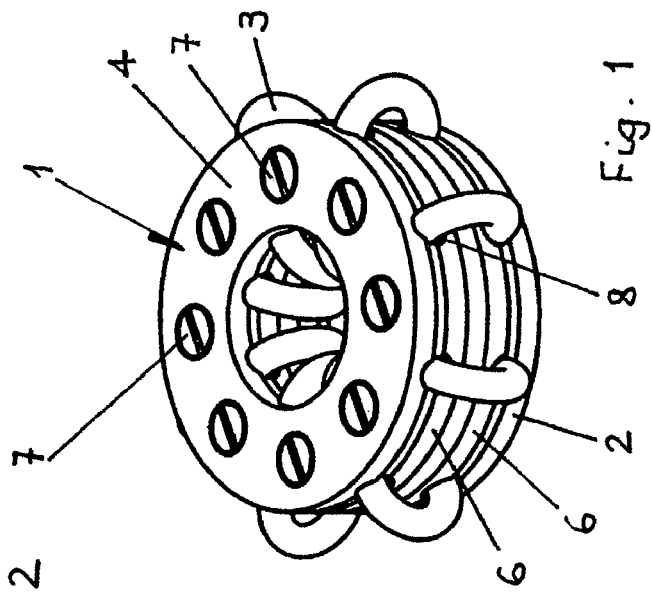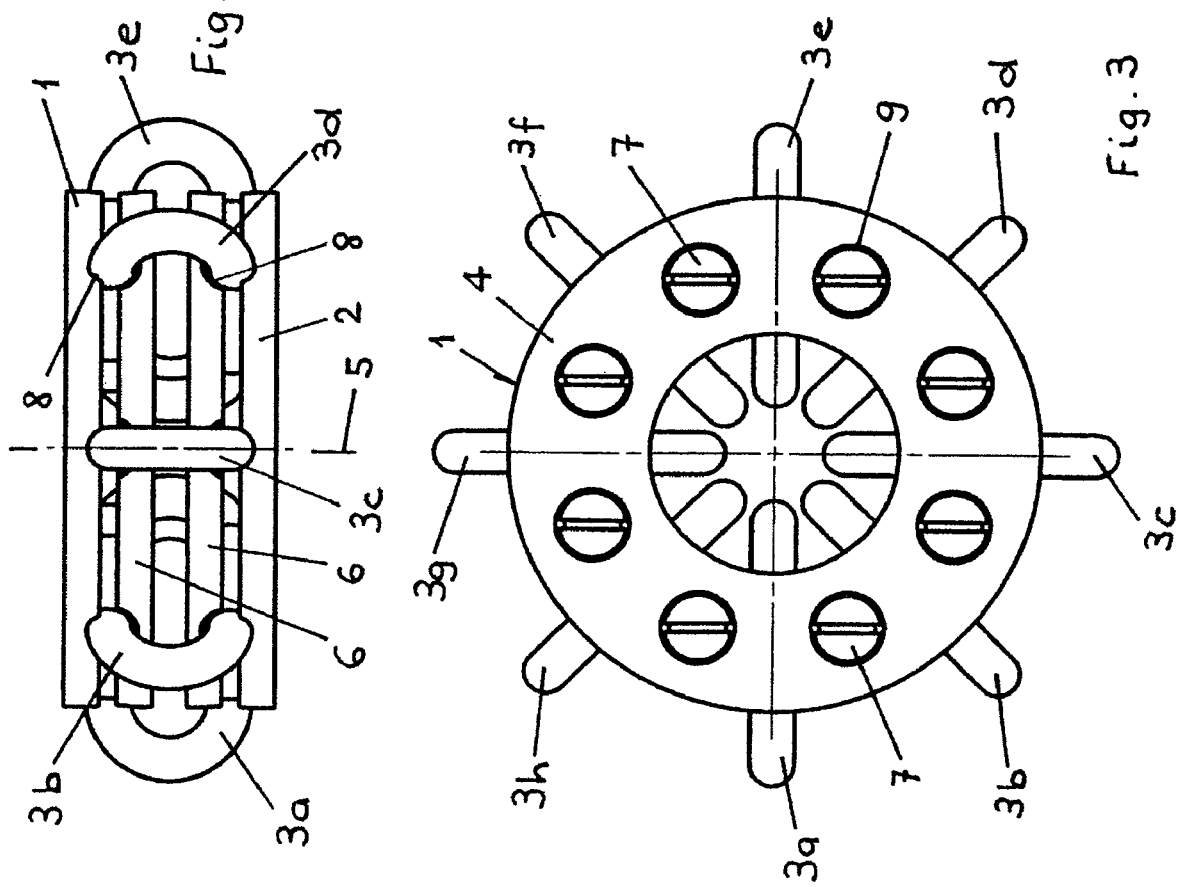

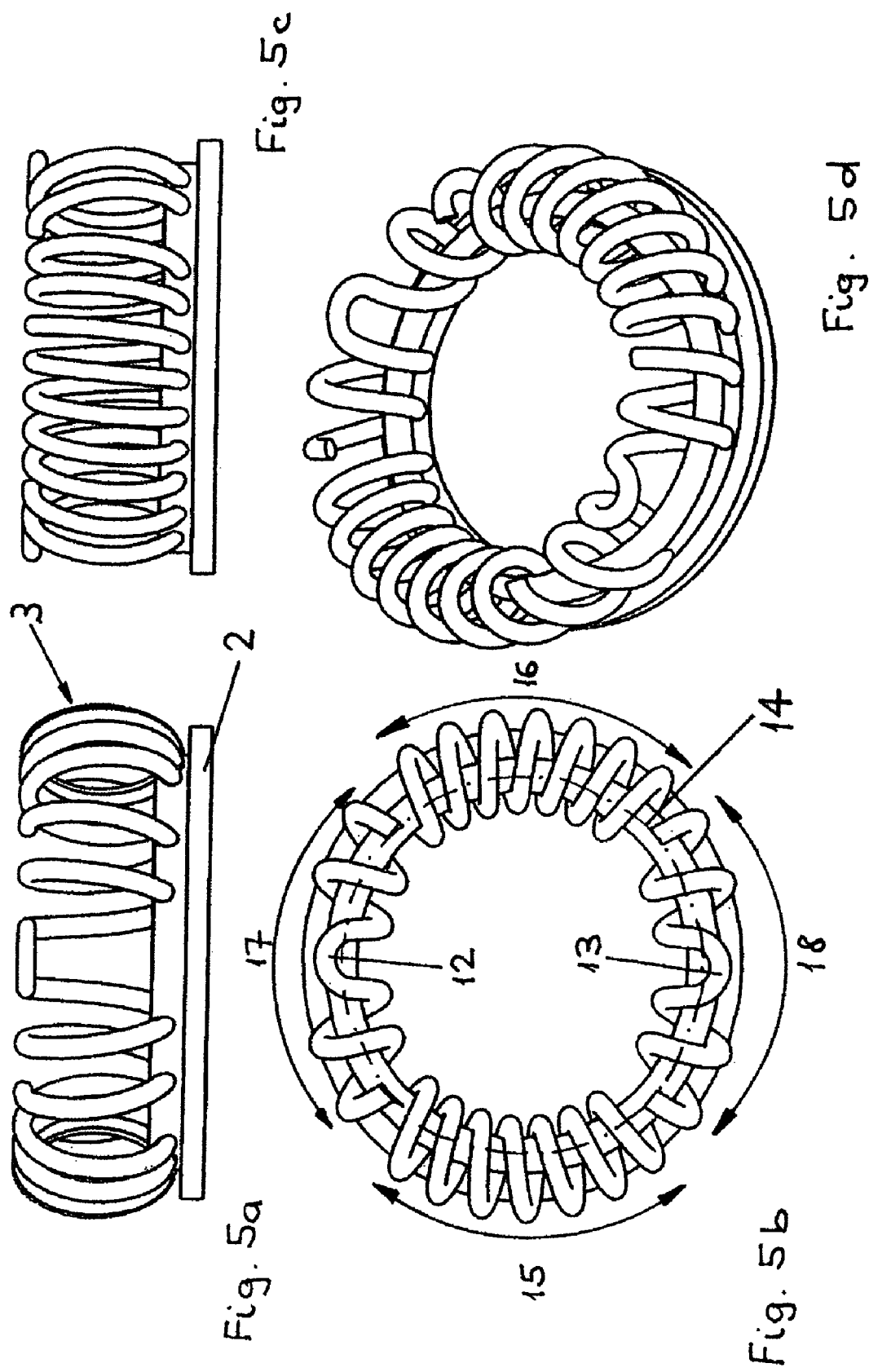

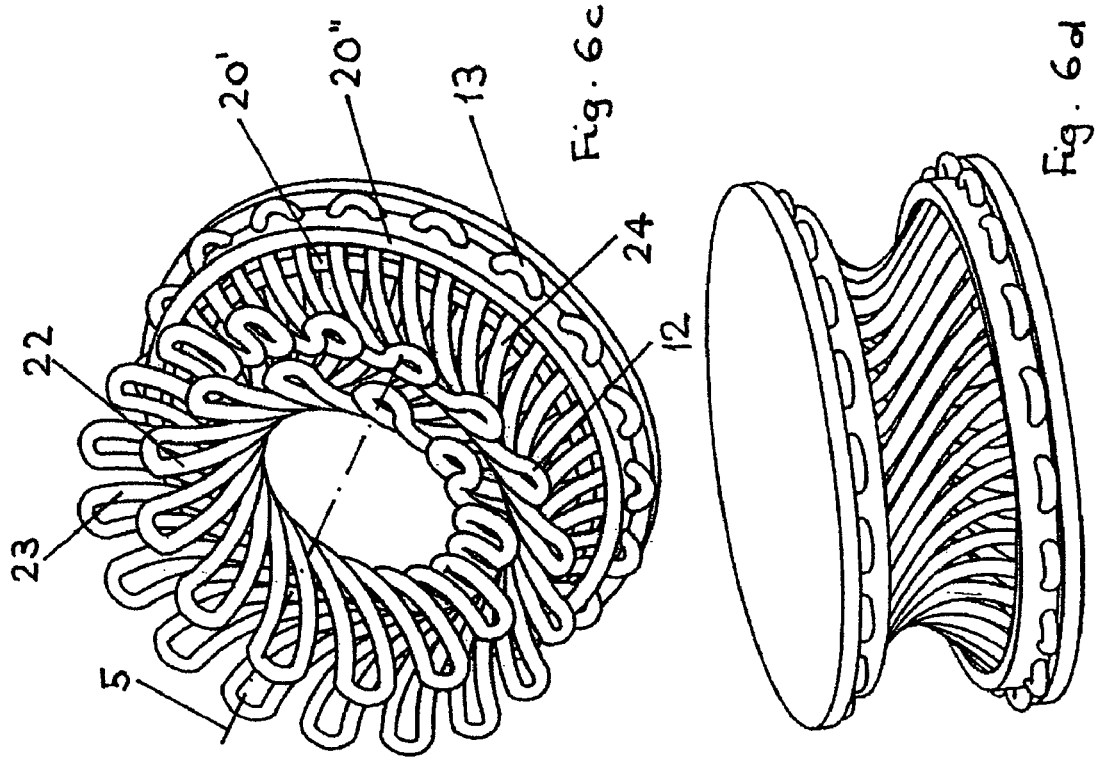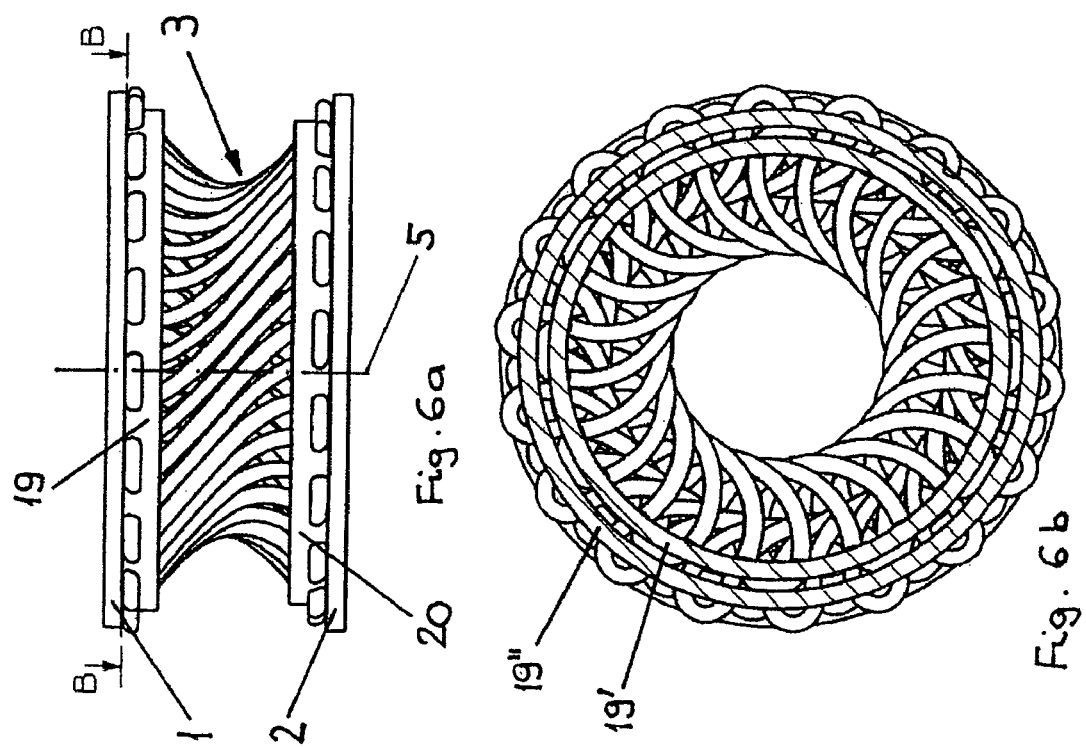

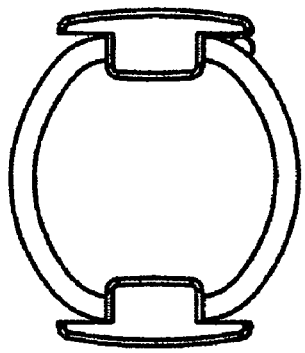
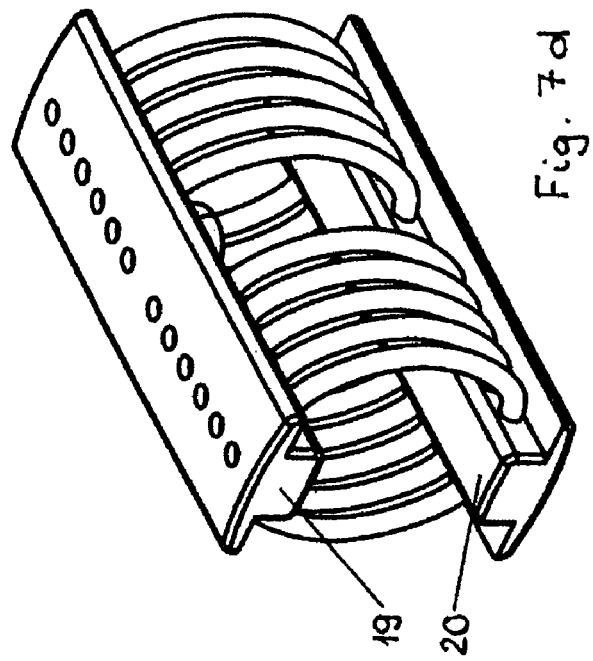
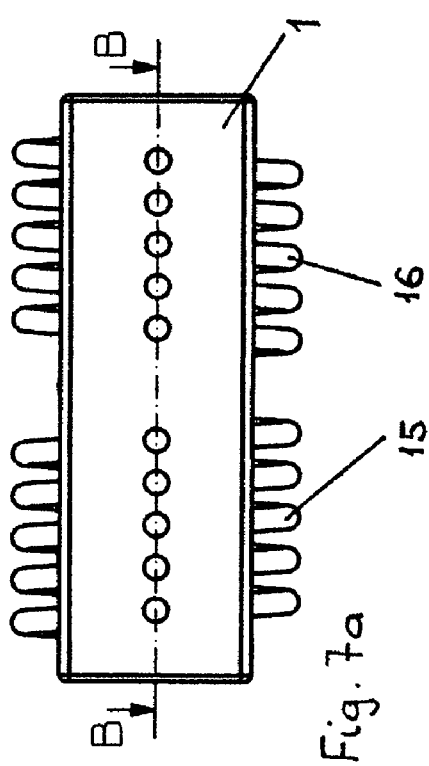
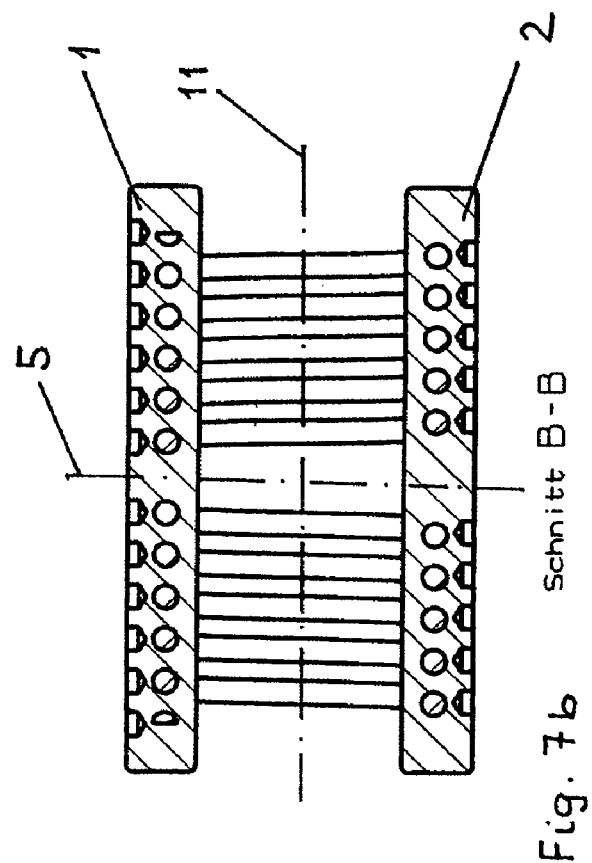

INTERVERTEBRAL DISC PROSTHESIS

CROSS-REFERENCE TO RELATED APPLICATIONS

This application is a continuation of International Application No. PCT/CH2003/00187, filed Mar. 24, 2003, the entirety of which is expressly incorporated by reference herein.

FIELD OF THE INVENTION

The present invention relates to a vertebral disc or intervertebral disc prosthesis, hereafter simply called intervertebral disc prosthesis. Such prostheses may be used as nucleus replacements, flexible cages or intervertebral disc prostheses, and are inserted posteriority (PLIF technique). When in the form of dynamic implants, they also may be emplaced between the dome extensions of adjacent vertebral discs.

BACKGROUND OF THE INVENTION

U.S. Pat. No. 5,458,642 (Beer) discloses an intervertebral disc prosthesis comprising an upper and a lower kidneys-shaped plate, these plates being each peripherally connected (about a central core) to each other by a plurality of helical springs. The helical springs are configured in equidistant manner to each other and allow displacing said plates in three dimensions within given limits. However this known intervertebral disc prosthesis incurs the drawback that the stiffness of the implant is identical in every radial direction—at the same distance from the implant center, in other words, the implant is symmetrically stiff.

SUMMARY OF THE INVENTION

The objective of the present invention is palliation. The present invention creates an intervertebral disc prosthesis exhibiting asymmetrical stiffness. Thereby the intervertebral disc prosthesis advantageously may be matched by design to physiological behavior so that for instance rearward spinal column extension shall be met by more stiffness than a forward lateral displacement. The present invention solves this problem by an intervertebral disc prosthesis.

The advantages of the present invention substantially are that its prosthesis enables physiological behavior when the spinal column is stressed and that in particular the implant center of rotation may be controlled by the asymmetric change in stiffness. In a preferred embodiment mode, the number of elastic devices is between 4 and 12, in particular between 6 and 10.

In another embodiment mode, the elastic devices are mutually identical but are configured radially unequally in the peripheral zones of the intervertebral disc prosthesis. This design offers the advantage that the rigidity, i.e. stiffness of said intervertebral disc prosthesis can be selectively set in production by using a variable number of identical elastic elements per unit peripheral angle or alternatively an irregular array (namely more or less dense) of elastically identical elements may be used in a manner that a different intervertebral disc prosthesis stiffness shall result depending on radial direction, said variable stiffness thereby better matching anatomical particulars than is the case for such conventional prostheses exhibiting symmetrical stiffness.

In still another embodiment mode, at least a portion of the elastic devices is different from one another, said devices however preferably being configured radially uniformly in the peripheral zone of the intervertebral disc prosthesis.

In a further embodiment mode of the present invention, at least one portion of the elastic devices is different, these elastic devices being configured in radially varying manner in the intervertebral disc prosthesis' peripheral zones.

In another further embodiment mode said intervertebral disc prosthesis exhibits higher stiffness in a sub-zone of a peripheral arc of 90° than in the complementary arc of 90°.

In a further embodiment mode, at least a part of the elastic elements is made of materials of different stiffnesses.

Appropriate materials are all known implant materials of a metallic or polymeric nature. Moreover the implant may be fitted with an HAC coating.

Preferred implant materials are titanium, nitinol, titanium alloys and steel. The following are preferred material combinations: for apposition plates: titanium/titanium alloys—for intermediate plates: titanium/titanium alloys—for screws: titanium—for rings: nitinol, titanium or steel.

The apposition plate geometry and surface shall appropriately match the natural end plates of the vertebras, the two apposition plates being optionally circular, rectangular, kidney-shaped, oval, spiral/helical in the various embodiment modes.

In yet a further embodiment, the elastic devices are rings or partial rings, the ring plane of such elements optionally being such that: the ring plane intersects the central axis of the intervertebral disc prosthesis; the ring plane does not intersect the central axis of the intervertebral disc prosthesis; the ring plane is substantially perpendicular to the two apposition plates; or the ring plane is oblique to the two apposition plates.

In another embodiment, at least part of the rings exhibit different stiffnesses, these rings preferably being configured in sequence with increasing respectively decreasing stiffness.

In yet another embodiment, the rings are arrayed peripherally, thereby offering the advantage of several peripheral sub-zones of higher and of lower stiffness.

Said elastic devices may be selected from the following materials in various embodiment modes: spiral/helical springs, elastic bellows, plastic cylinders, tapes/bands, wire mesh lattices, endless fibers, or plastic coated wires. Such designs offer the following advantages over the designs involving annular elastic devices: increased flexibility, simpler production know-how, easier handling; and visco-elastic behavior of the intervertebral disc prosthesis.

In a further embodiment mode, the elastic devices are made of a wire rope which preferably is a unifilament.

In further embodiments, the elastic devices include at least one spring element consisting of a spring wire designed as follows: the spring wire is fitted with serpentines, and/or the spring wire exhibits at least one loop.

In still another embodiment, the intervertebral disc prosthesis comprises a plastic core. Such a feature offers the significant advantages that said prosthesis exhibits visco-elastic behavior and that the motions of the adjacent vertebras are better damped.

In another embodiment of the present invention, the intervertebral disc prosthesis' viscosity is at least 0.7 mm at the periphery, preferably at least 1.0 mm and at most 1.2 mm, preferably at most 3.5 mm.

The elastic devices connected to the apposition plates may be geometrically locking, i.e. positively locking, or they may be frictionally locking.

In still another embodiment of the present invention, the two apposition plates subtend between them an angle of 10° to 14°.

In a further embodiment of the invention, the elastic devices are combined into one unit, the apposition plates being slipped onto or snapped onto said unit.

BRIEF DESCRIPTION OF THE DRAWINGS

The present invention and further developments of it are elucidated below by means of several illustrative embodiments and in relation to the partly schematic Figures.

FIG. 1 is a perspective view of an intervertebral disc prosthesis,

FIG. 2 is a side view of the intervertebral disc prosthesis of FIG. 1,

FIG. 3 is a top view of the intervertebral disc prosthesis of FIG. 1,

FIG. 5a is a front view of a further intervertebral disc prosthesis embodiment less the upper apposition plate, FIG. 5b is a top view of the intervertebral disc prosthesis of FIG. 5a, FIG. 5c is a side view of the intervertebral disc prosthesis of FIGS. 5a and 5b, FIG. 5d is a perspective view of the intervertebral disc prosthesis embodiment of FIGS. 5a through 5c, FIG. 6a is an elevation of another intervertebral disc prosthesis embodiment, FIG. 6b is a section B-B through the intervertebral disc prosthesis embodiment of FIG. 6a, FIG. 6c is a perspective view of the spring elements connected to the lower apposition plate of the intervertebral disc prosthesis embodiment of FIGS. 6a and 6b less the upper apposition plate, FIG. 6d is a perspective of the intervertebral disc prosthesis of FIGS. 6 through 6c, FIG. 7a is a top view of a further intervertebral disc prosthesis embodiment, FIG. 7b is a section B-B of the intervertebral disc prosthesis embodiment of FIG. 7a, FIG. 7c is a side view of the intervertebral disc prosthesis embodiment of FIGS. 7a and 7b, FIG. 7d is a perspective view of the intervertebral disc prosthesis embodiment of FIGS. 7a through 7c, FIG. 8 schematically shows two intervertebral disc prostheses such as shown in FIGS. 7a through 7d that are implanted between two vertebras.

DETAILED DESCRIPTION OF THE INVENTION

Figure 4A:
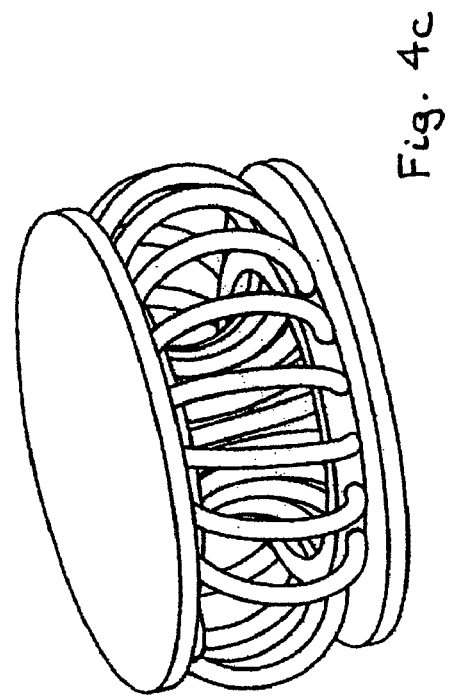
FIG. 4a is a side view of another embodiment mode of the intervertebral disc prosthesis.
Figure 4C:
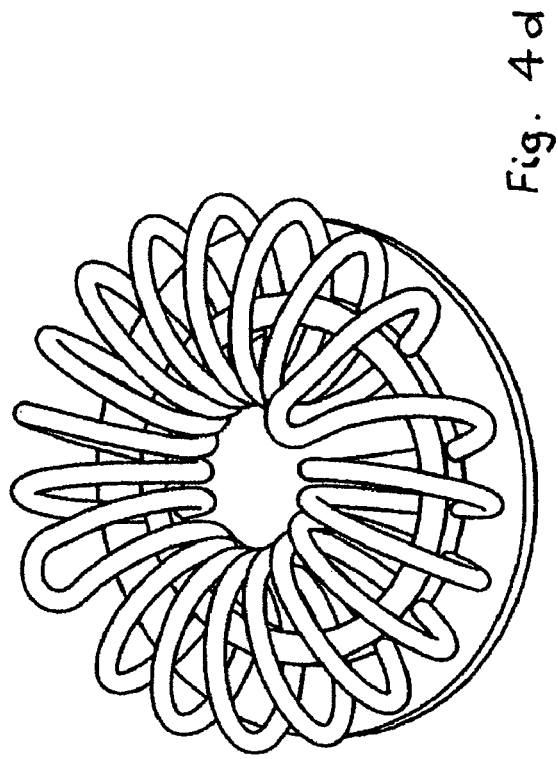
FIG. 4c is a perspective view of the intervertebral disc prosthesis embodiment of FIG. 4a, FIG. 4d is a perspective of intervertebral disc prosthesis embodiment of FIGS. 4a through 4b less the upper apposition plate.
Figure 4B:
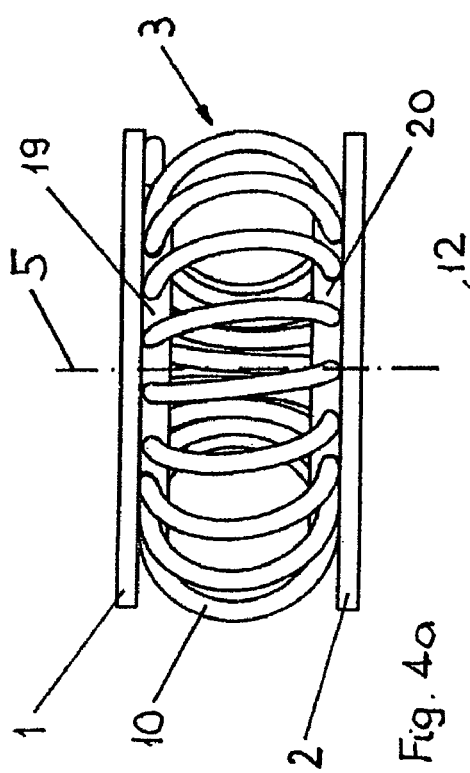
FIG. 4b is a top view of the intervertebral disc prosthesis of FIG. 4a less the upper apposition plate.
Figure 4D:
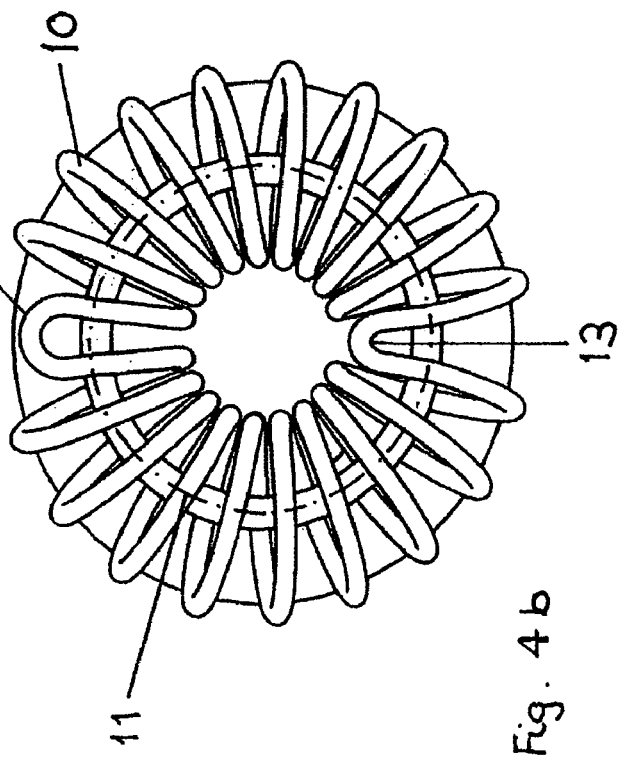

The intervertebral disc prosthesis shown in FIGS. 1 through 3 consists of an upper, circular apposition plate 1 suitable to come to rest against the base plate of a vertebra, further of a lower annular apposition plate 2 which is appropriate to come to rest against the cover plate of a vertebra, further two intermediate plates 6 which are configured between the two apposition plates 1, 2 and which are also circular, all plates being mounted perpendicularly to a common central axis 5.

A total of eight elastic devices 3 in the form of rings 3a-3h are configured between the two circular apposition plates 1, 2 and said devices run radially to the central axis 5, their annular plane being perpendicular to the apposition plates 1, 2.

In order that the intervertebral disc prosthesis be held together, the upper apposition plate 1 is connected to the adjacent intermediate plate by a total of eight screws 7 and in turn the lower apposition plate 2 is connected to its adjacent intermediate plate 6 by a total of eight screws 7. Accordingly the apposition plates 1, 2 comprise corresponding boreholes 9 receiving the screw heads and the intermediate plates 6 are fitted with corresponding threaded boreholes receiving the screw shanks. The screws 7 are always configured between two adjacent rings.

The individual rings 3a-3h are diametrically captured by the above described pair of plates 1, 6 and by the lower pair of plates 2, 6 in a manner that the two pairs of plates 1, 6 and 2, 6 are connected to each other by the rings 3a-3h and that, thanks to the elasticity of these rings 3a-3h, they may be moved from the parallel state when unstressed into a mutually slanted state within given limits (compressibility of about 1.0 to 1.5 mm at the periphery). As a result the two apposition plates 1, 2 may subtend between them an angle approximately of 12°.

In order to minimize the height of the intervertebral disc prosthesis, the apposition plates 1, 2 and the intermediate plates 6 may comprise clearances 8 matching the contours of the rings 3a-3h in the regions of the ring crossings.

The elastic rings 3a-3h are peripherally apart at regularly equidistant angles of 45° but exhibit different elasticities and stiffnesses, this feature being attained by using different materials, different ring geometries or different ring cross-sections (solid, hollow, round, rectangular). Consequently higher stiffness is attained in the zone of the rings 3b, 3c and 3d than in the zone of rings 3f, 3g and 3h. When a given force is applied perpendicularly to the apposition plate 1 to the zone of the ring 3c, then less compression shall be incurred (reduction of the distance between the two apposition plates 1, 2 than when the same force is applied to the zone of the ring 3g. This asymmetrical behavior results in improved physiological behavior of the intervertebral disc prosthesis in that, when the spinal column is bent forward, compression of the rings 3f, 3g and 3h shall be larger than the compression of the rings 3b, 3c and 3d if the spinal column were bent backward.

The spring constants of the individual rings may appropriately vary between 50 and 100%. Thus the spring constants may vary between 300 N/mm and 1,000 N/mm.

FIGS. 4a through 4d illustrate an embodiment mode wherein the elastic devices 3 are a helical spring 10 of which the longitudinal axis 11 is circular in a plane orthogonal to the central axis 5, as a result of which the helical spring 10 encloses the implant central axis 5 by an angle of 360°. In this design the helical spring 10 has been shifted by such a distance toward the periphery of the circular apposition plates 1, 2 that it does slightly project beyond said periphery. The helical spring 10 comprises two arcuate portions exhibiting opposite pitches/number of turns per unit length of the spring wire. The turns of the helical spring 10 between said two portions are connected to each other by a loop 12, 13. In this embodiment the loops 12, 13 are configured at those circumferential segments of the helical spring 10 which point toward the upper apposition plate 1. This design of the helical spring 10 exhibiting two arcuate portions of opposite turn pitches allows controlling the implant's impedance to torsion. Circular elevations 19, 20 concentric with the central axis 5 are present at the mutually opposite inner surfaces of the apposition plates 1, 2. For each turn, the spring wire passes once through boreholes in each of the two circular elevations 19, 20, and as a result the apposition plates 1, 2 and the helical spring 10 are firmly held together. Moreover the two loops 12, 13 are different form one another regarding the space they occupy between the two adjoining spring wire turns. In each arcuate portion of the helical spring 10, the turns exhibit a constant pitch, as a result of which the implant spring constant differs in value only at the junctions of the two arcuate portions of the helical spring 10. By means of the design of the two portions of opposite turn pitches of the helical spring 10, the invention offers equal implant torsion impedance in both directions of rotation.

The embodiment mode shown in FIGS. 5a through 5d differs from that of FIGS. 4a through 4d merely in that the apposition plates 1, 2 (only apposition plate 2 being shown) are oval and as a result the elastic devices 3 comprise 4 arcuate but separate helical spring elements 15, 16, 17, 18 configured along an oval longitudinal axis 14. Every two mutually diametrically opposite helical spring elements 15, 16, 17, 18 are mirror-symmetrical, two helical spring elements 15, 16 exhibiting turns of opposite pitches and the other two mirror-symmetrically configured helical spring elements 17, 18 each comprising at their midsts a loop 12, 13 entail a change in the direction of rotation of the turns. Furthermore the pitches of the two pairs of mirror-symmetrically configured helical spring elements 15, 16, 17, 18 are different, whereby the spring constants of the elastic devices 3 will be different depending on the position of the axis of rotation between the two vertebras 34, 35 (FIG. 8) adjoining the two apposition plates 1, 2.

FIGS. 6a through 6d show an embodiment mode of which the design of the elastic devices 3 differs from that of the embodiment mode shown in FIGS. 4 and 5 merely in that it comprises two spring elements 22, 23 concentric with the central axis 5, each spring element comprising a spring wire 25 exhibiting several serpentines 24. The spring elements 22, 23 are in the form of partly toroidal surfaces, the junction between the loops 12, 13 of the serpentines 24 running obliquely to the torus meridians. The angles between the torus meridians and the junctions between the loops 12, 13 of the serpentines 24 of the two spring elements 22, 23 are opposite and of equal magnitude. Also each apposition plate 1, 2 comprises two elevations 19', 19'', 20', 20'' concentric with the central axis 5. Similarly to the case of the embodiments of FIG. 4, each loop 12 of a serpentine 24 passes through two boreholes in one of the circular elevations 19 at the upper apposition plate 1, whereas the other loop 13 of the serpentine 24 passes through two boreholes in one of the circular elevations 20 at the lower apposition plate 2, as a result of which the two apposition plates 1, 2 and the elastic devices 3 are held together. The loops 12, 13 of the inner spring element 22 pass through boreholes in the inner elevations 19', 20' and the loops 12, 13 of the outer spring element 23 pass through the boreholes in the outer elevations 19'', 20''.

FIGS. 7a through 7d show an embodiment mode comprising an upper and a lower apposition plate 1, 2 fitted with rectangular surfaces transverse to the central axis 5. The longitudinal axis 11 of two, in-series helical spring elements 15, 16 between the apposition plates 1, 2 is parallel to the long axes of the rectangular apposition plates 1, 2. The two helical spring elements 15, 16 exhibit mutually opposite turn pitches. Elevations 19, 20 parallel to the long axes moreover are configured at the inside surfaces of the apposition faces 1, 2 and are fitted with boreholes running transversely to the said long axes. The turns of the helical screw elements 15, 16 passing through said boreholes therefore hold together the two apposition plates 1, 2.

Figure 8:
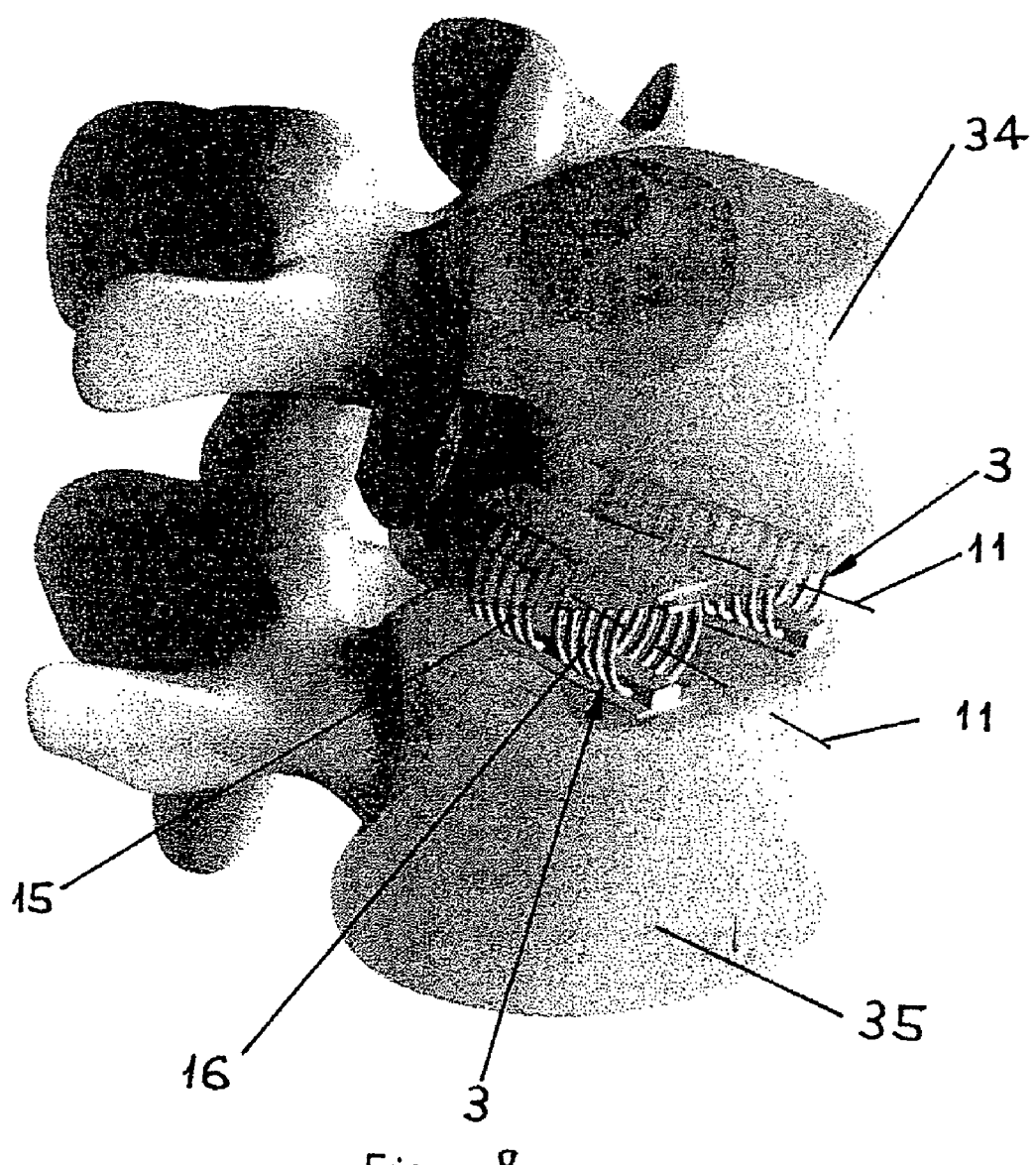
Figure 9:
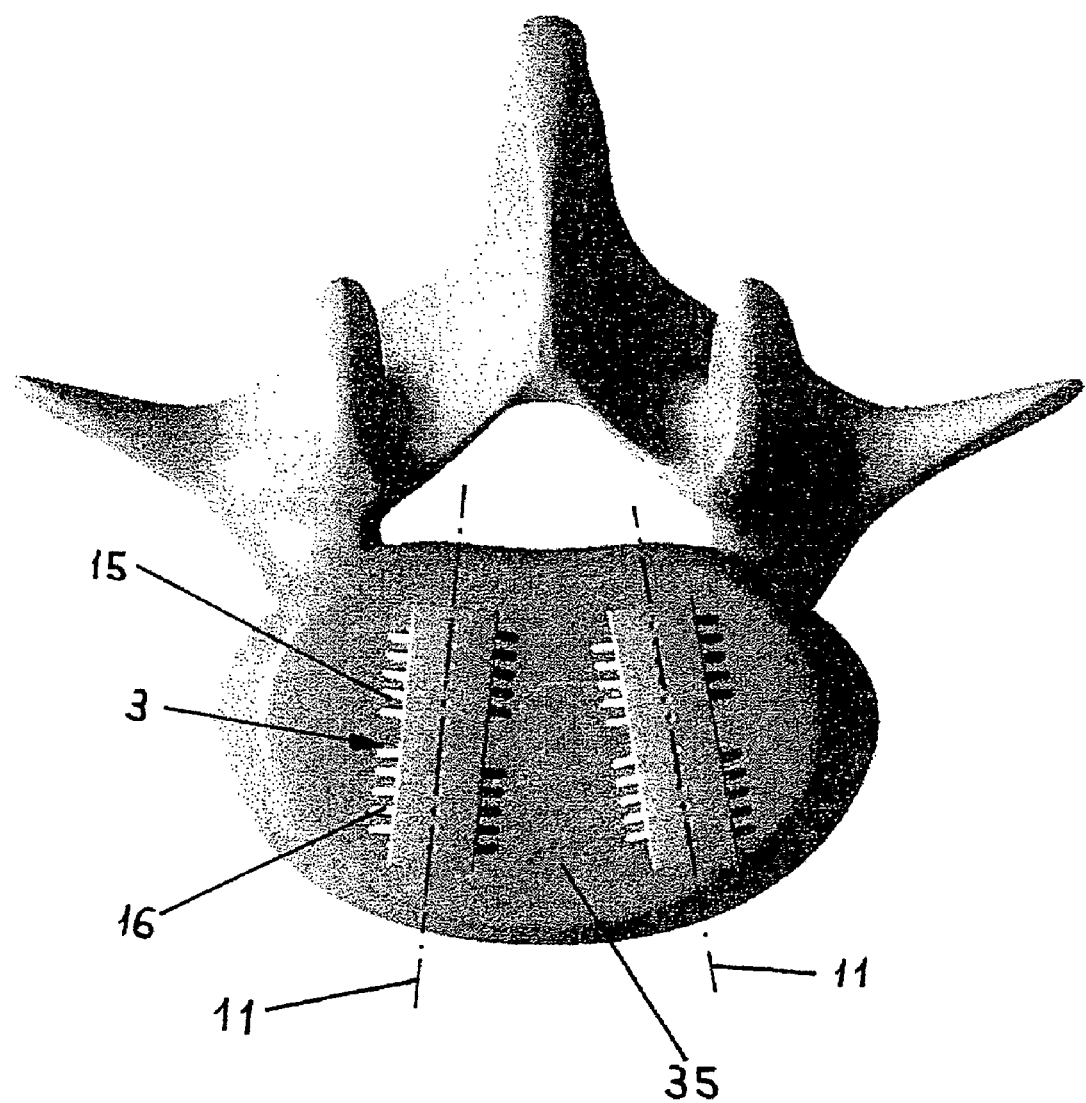
FIG. 9 is a top view parallel to the axis of the spinal column of the upper plate of a vertebra with two intervertebral disc prostheses such as shown in FIGS. 7a through 7d.
Figure 10:
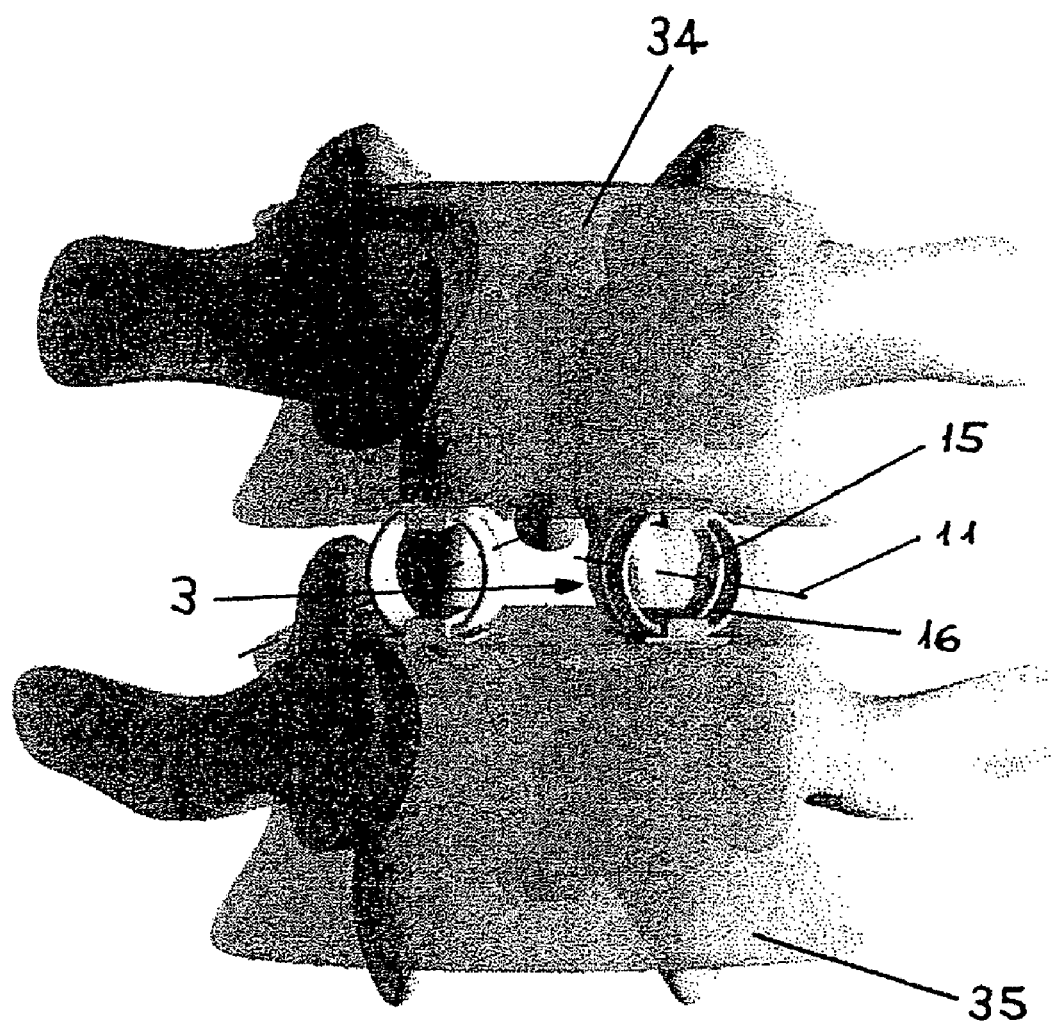
FIG. 10 is an elevation of two intervertebral disc prostheses such as are shown in FIGS. 7a through 7d implanted between two vertebras.

FIGS. 8 through 10 illustrate how to use two intervertebral disc prostheses such as are shown in FIGS. 7a through 7d. The two intervertebral disc prostheses are inserted into intervertebral space of two mutually adjoining vertebras 34, 35 in a manner that the longitudinal axes 11 of the helical spring elements 15, 16 run from anterior to posterior, each intervertebral prosthesis being mounted laterally to the longitudinal axis of the spinal column. This configuration of the intervertebral disc prostheses offer differential spring constants of the elastic devices 3 for the flexion/extension and lateral bending of the spinal column.

Figure 11:
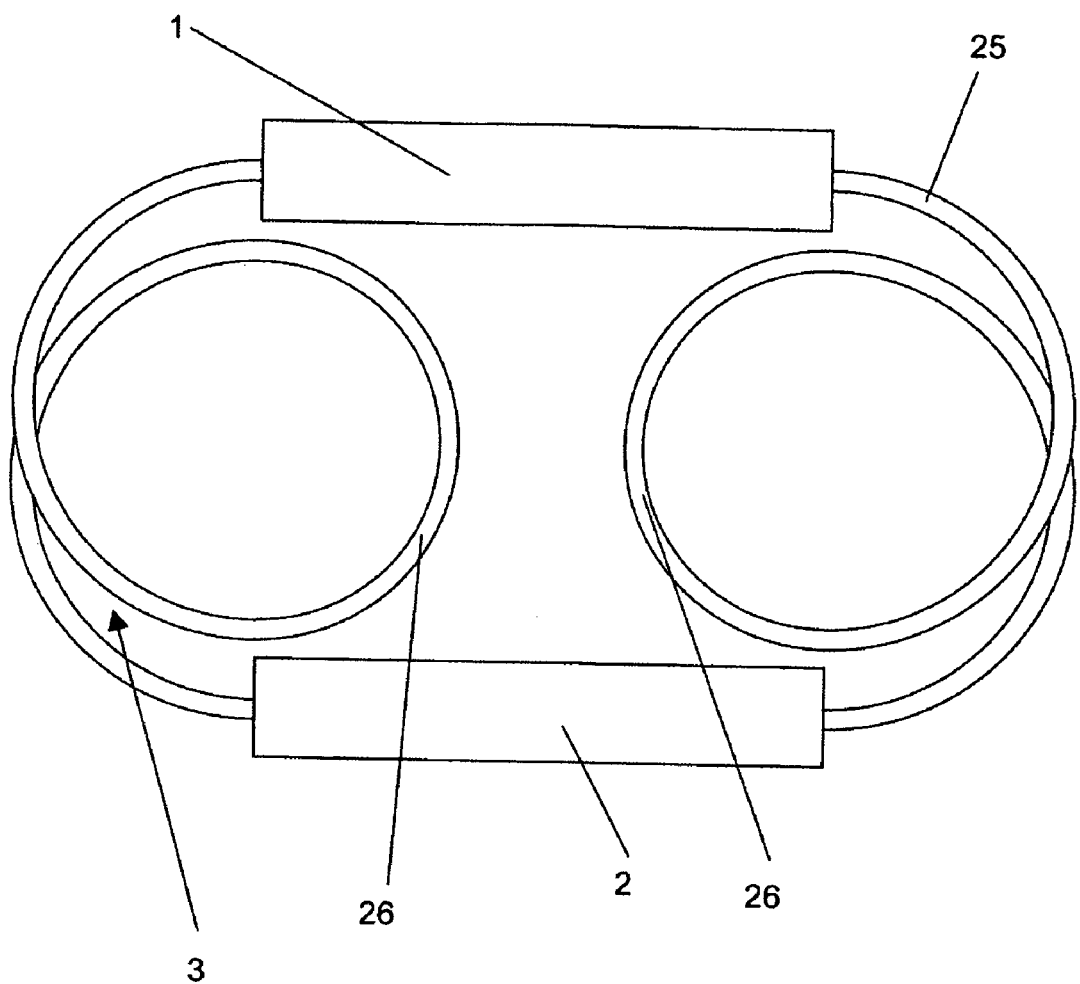
FIG. 11 is an elevation of another embodiment of the elastic devices of the intervertebral disc prosthesis of the invention.

FIG. 11 shows an embodiment mode of the elastic devices 3 including a spring wire 25 wound into loops 26. The loops 26 on the spring wire 25 may be so designed on one hand that similarly to the case of the rings of FIG. 1 they shall be closed and constitute individual spring elements which, in a desired manner, shall be distributed between the apposition plates 1, 2. On the other hand and similarly to the design shown in FIG. 4, the loops 26 may constitute the turns of a kind of helical-spring element. The anchoring of the spring wire 25 onto the apposition plates 1, 2 may be carried out in the manner of any embodiment shown in FIGS. 1 through 10. Also, the design of the apposition plates 1, 2 as well as the distribution of the elastic devices 3 is carried out in the manner of any embodiment mode illustrated in FIGS. 1 through 10.

What is claimed is:

1. An intervertebral disc prosthesis having a longitudinal axis, the prosthesis comprising:
    a first plate having a first plate longitudinal axis, the first plate configured to engage a first vertebrae;
    a second plate having a second plate longitudinal axis, the second plate configured to engage a second vertebrae; and
    first and second helical spring elements disposed at least partially between the first and second plates, the first and second helical spring elements being coaxially aligned in a series along the longitudinal axis of the prosthesis, each of the first and second helical spring elements including a lumen defining a longitudinal axis such that the longitudinal axis of the first and second helical spring elements, the first plate longitudinal axis and the second plate longitudinal axis are all parallel to the longitudinal axis of the prosthesis;
    wherein the first helical spring element has a first stiffness, and the second helical spring element has a second stiffness; and wherein the first stiffness is greater than the second stiffness.

2. The prosthesis of claim 1, wherein the first helical spring element is comprised of a different material than the second helical spring element.

3. The prosthesis of claim 1, wherein the first and second helical spring elements are substantially equally sized.

4. The prosthesis of claim 1, wherein the first and second helical spring elements have substantially different cross-sections.

5. The prosthesis of claim 1, wherein the first helical spring element is more tightly coiled than the second helical spring element.

6. The prosthesis of claim 1, wherein the first and second plates are rectangular.

7. The prosthesis of claim 1, wherein the first and second helical spring elements have mutually opposite turn pitches.

8. The prosthesis of claim 1, wherein the first and second helical spring elements each include a plurality of turns and the first and second plates each include an elevation extending from an inner surface thereof, the elevation being parallel to the longitudinal axis of the prosthesis, each elevation including a plurality of boreholes running transversely to the longitudinal axis of the prosthesis, each borehole receiving one of the turns of the first and second helical spring elements.

* * * * *